US012590943B2

(12) United States Patent (10) Patent No.: US 12,590,943 B2
Seike et al. (45) Date of Patent: Mar. 31, 2026

(54) LIQUID SENSOR AND HYDRAULIC UNIT

(71) Applicant: DAIKIN INDUSTRIES, LTD., Osaka (JP)

(72) Inventors: Hikaru Seike, Osaka (JP); Hirokazu Nakamura, Osaka (JP); Mineo Inoue, Osaka (JP); Kenji Ayado, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 464 days.

(21) Appl. No.: 17/611,006

(22) PCT Filed: May 14, 2020

(86) PCT No.: PCT/JP2020/019288
§ 371 (c)(1),
(2) Date: Nov. 12, 2021

(87) PCT Pub. No.: WO2020/230855
PCT Pub. Date: Nov. 19, 2020

(65) Prior Publication Data
US 2022/0228983 A1    Jul. 21, 2022

(30) Foreign Application Priority Data

May 16, 2019    (JP) ................................. 2019-092976
May 16, 2019    (JP) ................................. 2019-092977
May 16, 2019    (JP) ................................. 2019-092979

(51) Int. Cl.
*G01N 33/28*    (2006.01)
*G01F 23/02*    (2006.01)
(Continued)

(52) U.S. Cl.
CPC ......... *G01N 33/2888* (2013.01); *G01F 23/02* (2013.01); *G01F 23/292* (2013.01);
(Continued)

(58) Field of Classification Search
CPC .... G01N 21/25; G01N 21/251; G01N 21/255; G01N 21/27; G01N 21/29;
(Continued)

(56) References Cited

U.S. PATENT DOCUMENTS 2,295,366 A * 9/1942 Stout .................... G01N 21/534
210/85
3,710,111 A * 1/1973 Collura .................. G01N 21/33
250/301
(Continued)

FOREIGN PATENT DOCUMENTS

CN        102252726 A    11/2011
CN        103380365 A    10/2013
(Continued)

OTHER PUBLICATIONS

European Search Report of corresponding EP Application No. 20 80 5503.8 dated Dec. 9, 2022.
(Continued)

*Primary Examiner* — Gordon J Stock, Jr.
(74) *Attorney, Agent, or Firm* — Spencer Fane LLP

(57)    ABSTRACT

A liquid sensor includes a light receiver configured to receive light. The light receiver is attachable to an outside of an accommodation unit into which a liquid is introduced and which has translucency. The light receiver receives light that has passed through the liquid in the accommodation unit or light reflected by the liquid, and outputs a signal related to a physical quantity of the liquid.

15 Claims, 10 Drawing Sheets

(51) Int. Cl.

| | |
|---|---|
| *G01F 23/292* | (2006.01) |
| *G01F 23/30* | (2006.01) |
| *G01F 23/68* | (2006.01) |
| *G01F 23/70* | (2006.01) |
| *G01N 21/27* | (2006.01) |
| *G01N 21/55* | (2014.01) |
| *G01N 21/59* | (2006.01) |
| *G01N 21/85* | (2006.01) |
| *H10N 10/10* | (2023.01) |

(52) U.S. Cl.
CPC .......... *G01F 23/2928* (2013.01); *G01F 23/30* (2013.01); *G01F 23/686* (2013.01); *G01F 23/706* (2013.01); *G01N 21/27* (2013.01); *G01N 21/55* (2013.01); *G01N 21/59* (2013.01); *G01N 21/85* (2013.01); *H10N 10/10* (2023.02)

(58) Field of Classification Search
CPC .... G01N 21/3577; G01N 21/55; G01N 21/59; G01N 21/84; G01N 21/85; G01N 21/8507; G01N 33/2888; G01F 23/0007; G01F 23/0046; G01F 23/02; G01F 23/18; G01F 23/185; G01F 23/28; G01F 23/282; G01F 23/284; G01F 23/2845; G01F 23/292; G01F 23/2921; G01F 23/2922; G01F 23/2924; G01F 23/2925; G01F 23/2928; G01F 23/30; G01F 23/56; G01F 23/606; G01F 23/64; G01F 23/686; G01F 23/70; G01F 23/706
See application file for complete search history.

(56) References Cited

U.S. PATENT DOCUMENTS

| | | | | |
|---|---|---|---|---|
| 3,892,485 | A * | 7/1975 | Merritt | G01N 21/532 356/70 |
| 4,014,010 | A * | 3/1977 | Jinotti | G01F 23/706 604/122 |
| 4,306,525 | A * | 12/1981 | Faxvog | F01M 11/12 123/196 S |
| 4,570,069 | A * | 2/1986 | Gager | G01N 33/2888 356/70 |
| 4,649,281 | A * | 3/1987 | Schmitt | G01N 33/1833 210/194 |
| 4,695,796 | A * | 9/1987 | Omet | G01D 5/344 324/207.13 |
| 4,920,336 | A * | 4/1990 | Meijer | A61M 5/1684 250/577 |
| 5,049,742 | A * | 9/1991 | Hosonuma | F16N 29/00 356/70 |
| 5,175,438 | A | 12/1992 | Ikeda | |
| 5,194,910 | A * | 3/1993 | Kirkpatrick, Jr. | G01N 21/3151 356/70 |
| 5,581,086 | A * | 12/1996 | Ben-Menachem | G01N 21/3577 250/343 |
| 5,950,487 | A * | 9/1999 | Maresca, Jr. | G01F 23/686 250/577 |
| 6,333,512 | B1 | 12/2001 | Wirthlin | |
| 6,529,751 | B1 * | 3/2003 | Van Driel | A61M 1/3626 604/122 |
| 6,664,558 | B1 * | 12/2003 | Barbier | G01F 23/2921 250/577 |
| 6,964,278 | B2 * | 11/2005 | Tschanz | G01F 23/02 73/304 C |
| 7,116,236 | B2 * | 10/2006 | Denietolis, Jr. | G01F 23/2921 73/290 R |

| | | | | |
|---|---|---|---|---|
| 7,605,361 | B2 * | 10/2009 | Uchida | G01N 21/3577 356/135 |
| 7,612,874 | B2 * | 11/2009 | Kong | G01N 21/314 356/70 |
| 7,661,294 | B2 * | 2/2010 | Dam | A61M 1/3626 73/598 |
| 9,046,502 | B2 * | 6/2015 | Chikamune | G01N 21/78 |
| 9,063,075 | B2 * | 6/2015 | Gorritxategi | G01N 21/25 |
| 9,383,315 | B2 * | 7/2016 | Cheim | G01N 21/33 |
| 9,658,153 | B2 * | 5/2017 | Goto | G01N 1/00 |
| 9,851,295 | B2 | 12/2017 | Coates et al. | |
| 9,939,369 | B2 * | 4/2018 | Ida | G01N 21/8507 |
| 9,964,483 | B2 * | 5/2018 | Coates | G01N 21/94 |
| 9,995,726 | B2 * | 6/2018 | Shirata | G01N 21/25 |
| 10,234,326 | B2 * | 3/2019 | Kwon | G01F 23/0046 |
| 10,281,449 | B2 * | 5/2019 | Onuma | G01N 21/27 |
| 10,407,296 | B2 * | 9/2019 | Bjornebo | G01N 21/645 |
| 10,539,054 | B2 * | 1/2020 | Fitch | F01M 11/10 |
| 10,758,839 | B1 * | 9/2020 | Lantz | G01J 3/0202 |
| 10,801,958 | B2 * | 10/2020 | Goto | H10N 10/17 |
| 10,809,164 | B2 * | 10/2020 | Young | G01N 21/94 |
| 10,935,490 | B2 * | 3/2021 | Langhoff | G01N 21/253 |
| 10,976,201 | B2 * | 4/2021 | Morgan, III | G01N 21/51 |
| 10,983,044 | B2 * | 4/2021 | Metting | C11B 1/00 |
| 11,054,364 | B2 * | 7/2021 | Foster | G01N 21/255 |
| 11,378,437 | B2 * | 7/2022 | Boldt | G01F 25/17 |
| 11,442,019 | B2 * | 9/2022 | Morton | G01N 1/42 |
| 11,579,095 | B2 * | 2/2023 | Coates | G01J 3/00 |
| 2006/0192122 | A1 * | 8/2006 | Chen | G01N 21/3504 250/339.13 |
| 2009/0310138 | A1 * | 12/2009 | Vanhanen | G01N 33/2888 356/432 |
| 2013/0312497 | A1 | 11/2013 | Chikamune | |
| 2015/0167455 | A1 * | 6/2015 | Irani | E21B 49/081 73/152.23 |
| 2015/0323369 | A1 * | 11/2015 | Marquardt | G01F 23/802 73/290 R |
| 2015/0362350 | A1 * | 12/2015 | Miller | G01F 23/802 73/290 R |
| 2016/0252490 | A1 | 9/2016 | Shirata et al. | |
| 2018/0031407 | A1 * | 2/2018 | Kopansky | G01F 23/2922 |
| 2019/0128807 | A1 | 5/2019 | Goto et al. | |
| 2019/0242816 | A1 * | 8/2019 | Conner | G01N 27/06 |
| 2022/0146412 | A1 * | 5/2022 | Seike | G01N 33/2888 |

FOREIGN PATENT DOCUMENTS

| | | | | | |
|---|---|---|---|---|---|
| JP | 60-181513 | A | | 9/1985 | |
| JP | S6134308 | A | * | 2/1986 | |
| JP | 10-185659 | A | | 7/1998 | |
| JP | 3052909 | B2 | * | 6/2000 | |
| JP | 2001287100 | A | * | 10/2001 | |
| JP | 2005-156297 | A | | 6/2005 | |
| JP | 2008026125 | A | * | 2/2008 | |
| JP | 2009-2861 | A | | 1/2009 | |
| JP | 2010-2203 | A | | 1/2010 | |
| JP | 2015-232582 | A | | 12/2015 | |
| JP | 2017-198549 | A | | 11/2017 | |
| KR | 1999-0040786 | A | | 6/1999 | |
| KR | 20140001055 | A | * | 1/2014 | G08B 21/182 |
| KR | 20160120336 | A | * | 10/2016 | G01N 21/27 |
| WO | WO-2015045908 | A1 | * | 4/2015 | F03D 80/70 |
| WO | WO-2017002079 | A1 | * | 1/2017 | G01N 21/359 |

OTHER PUBLICATIONS

International Search Report of corresponding PCT Application No. PCT/JP2020/019288 dated Aug. 11, 2020.
International Preliminary Report of corresponding PCT Application No. PCT/JP2020/019288 dated Nov. 25, 2021.

* cited by examiner

*Fig. 8*

LIQUID SENSOR AND HYDRAULIC UNIT

CROSS-REFERENCE TO RELATED APPLICATIONS

This U.S. National stage application claims priority under 35 U.S.C. § 119 (a) to Japanese Patent Application Nos. 2019-092976, 2019-092977 and 2019-092979, filed in Japan on May 16, 2019.

BACKGROUND

Field of the Invention

The present disclosure relates to liquid sensors and hydraulic units.

Background Information

As a conventional liquid sensor, there is a liquid sensor which is installed in a machine and detects deterioration of lubricating oil in the machine (see JP 2015-232582 A).

SUMMARY

However, since the conventional liquid sensor is installed in a machine by screw connection, a sealing structure is required between the liquid sensor and the machine, and there is a problem that workability of attachment work is low.

The present disclosure proposes a liquid sensor and a hydraulic unit capable of improving workability of attachment work.

A liquid sensor of the present disclosure includes a light receiver configured to receive light. The light receiver is attachable to an outside of an accommodation unit into which a liquid is introduced and which has translucency. The light receiver receives light that has passed through the liquid in the accommodation unit or light reflected by the liquid, and outputs a signal related to a physical quantity of the liquid.

According to the liquid sensor of the present disclosure, since the light receiver is attachable to the outside of the accommodation unit into which the liquid to be measured is introduced, a seal structure for preventing leakage of a hydraulic oil introduced into the accommodation unit to the outside is not required between the liquid sensor and the accommodation unit, and workability of attachment work of the liquid sensor to the accommodation unit can be improved.

The translucency according to the present disclosure is translucency with respect to light passing through the liquid.

In one embodiment, the signal related to a physical quantity of the liquid includes a signal related to the deterioration degree of the liquid.

In one embodiment, the signal related to a physical quantity of the liquid includes a signal related to a hue of light that has passed through the liquid and has been received by the light receiver or light that has been reflected by the liquid and has been received by the light receiver. The deterioration degree of the liquid is determined from the hue.

In one embodiment, the signal related to a physical quantity of the liquid includes a signal related to presence or absence of the liquid in the accommodation unit.

In one embodiment, the accommodation unit includes a float disposed inside the accommodation unit.

In the above embodiment, when the float is at a level at which the light receiver is attached to the accommodation unit, the float blocks light and significantly changes the intensity of light received by the light receiver. This allows the accuracy of detection of the presence or absence of liquid can be improved.

The liquid sensor according to one embodiment includes:
a rechargeable power source configured to supply electric power to the light receiver, and
a thermoelectric conversion element configured to generate electric power for charging the power source.

In the above embodiment, since the liquid sensor includes a rechargeable power source that supplies power to the light receiver and a thermoelectric conversion element that generates power for charging the power source, wiring for supplying power from the outside to the liquid sensor is not required, and the liquid sensor is allowed to have a simplified wiring structure.

The liquid sensor according to one embodiment includes a wireless transmitter configured to be supplied with electric power from the power source and to transmit the signal related to a physical quantity of the liquid of the light receiver to outside.

According to the above embodiment, since there is no need for wiring for outputting the signal output by the light receiver to outside, the wiring structure can be simplified.

The liquid sensor according to one embodiment includes a light emitter configured to emit light. The light emitter is attachable to the outside of the accommodation unit. The light receiver receives light emitted by the light emitter and having passed through the liquid in the accommodation unit or light emitted by the light emitter and having been reflected by the liquid in the accommodation unit.

In one embodiment, the light emitter and the light receiver are arranged to face each other across the accommodation unit.

In general, in a transmission type sensor, a surface of the accommodation unit has less influence on the detection accuracy than in other types of photoelectric sensors. In the above embodiment, since the liquid sensor is a transmission type sensor in which the light emitter and the light receiver are arranged to face each other across the accommodation unit, it is possible to perform reliable detection as compared with a case where a sensor of another type is used as the liquid sensor.

In one embodiment, the light emitter and the light receiver are arranged on the same side with respect to the accommodation unit.

In general, in a reflective sensor, since a light emitter and a light receiver are arranged on the same side of an accommodating unit, the reflective sensor is smaller than other types of photoelectric sensors. In the above embodiment, since the liquid sensor is a reflective sensor in which the light emitter and the light receiver are arranged on the same side of the accommodation unit, the liquid sensor can be made smaller than a case where a sensor of another type is used as the liquid sensor.

The liquid sensor according to one embodiment includes a casing attachable to the outside of the accommodation unit. The light emitter and the light receiver are integrally provided in the casing.

In the above embodiment, when the light emitter and the light receiver are integrally provided in the casing in a state where the optical axis of the light emitter and an optical axis of the light receiver coincide with each other, it is not necessary to adjust the optical axes of the light emitter and the light receiver to align the optical axes, when the liquid sensor is attached, so that workability of attachment work of the liquid sensor to the accommodation unit can be improved.

In one embodiment, in the light emitter, a light emission manner, that is, a manner in which the light emitter emits light, is determined according to the signal related to a physical quantity of the liquid of the light receiver.

In the above embodiment, the liquid sensor notifies a user of information on the physical quantity of the liquid by the light emission manner of the light emitter. For example, when the detection result of the liquid sensor indicates an abnormality, the light emitter of the liquid sensor emits light in a light emission manner corresponding to the abnormality. In this way, so that the liquid sensor notifies the user that the liquid sensor has detected the abnormality. Thus, the user can easily recognize the information (for example, abnormality) on the physical quantity of the liquid to be measured by visually observing the light emission manner of the liquid sensor.

In addition, since the light emitter of the liquid sensor has both a function as a projector of a photoelectric sensor and a function of notifying the user according to the signal related to the physical quantity of the liquid, the structure of the liquid sensor can be simplified as compared with a case where these functions are separately provided.

In one embodiment, the accommodation unit is a liquid level gauge.

In general, a liquid level gauge is installed at a place where a user can easily visually observe the liquid level gauge. Therefore, according to the above embodiment, since the liquid sensor is attached to the liquid level gauge, the user can easily visually observe the light emitter of the liquid sensor, so that the user can easily recognize the information (for example, abnormality) on the physical quantity of the liquid to be measured.

In one embodiment, the light emitter changes its state from off to blinking or blinking to off according to the signal related to a physical quantity of the liquid.

In one embodiment, in the light emitter, the emission color changes according to the signal related to a physical quantity of the liquid.

A hydraulic unit of one embodiment includes the liquid sensor described above.

BRIEF DESCRIPTION OF DRAWINGS

FIG. 8 is a cross-sectional view similar to FIG. 3 according to a third embodiment of the present disclosure.

DETAILED DESCRIPTION OF EMBODIMENT(S)

Hereinafter, liquid sensors and hydraulic units according to embodiments of the present disclosure will be described with reference to the accompanying drawings.

First Embodiment

Figure 1:
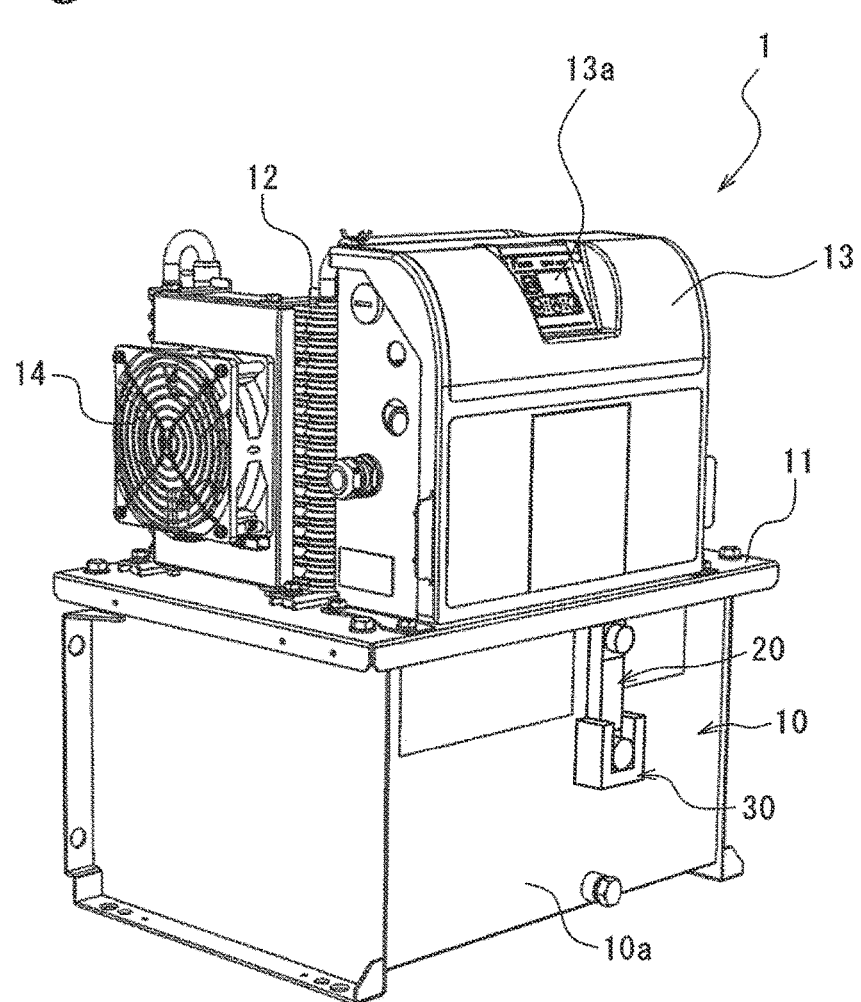
FIG. 1 is a perspective view of a hydraulic unit according to a first embodiment of the present disclosure.

FIG. 1 is a perspective view of a hydraulic unit 1 according to a first embodiment of the present disclosure. The hydraulic unit 1 according to the present embodiment supplies hydraulic oil to an external apparatus such as a machine tool.

Referring to FIG. 1, the hydraulic unit 1 includes a hydraulic oil tank 10 that accommodates hydraulic oil, and a mount 11 attached to an upper portion of the hydraulic oil tank 10. The hydraulic unit 1 includes a hydraulic pump (not shown), a motor (not shown) that drives the hydraulic pump, an oil cooler 12 that cools hydraulic oil discharged from the hydraulic pump, and a controller 13 that controls the motor. The hydraulic pump, the motor, the oil cooler 12, and the controller 13 are mounted on the mount 11, and the hydraulic oil tank 10 is disposed below the mount 11. In addition, the hydraulic unit 1 includes a cooling fan 14 that supplies cooling air to the motor and the oil cooler 12. The hydraulic unit 1 is herein described by way of example only; and not limited to the above-described structure.

A liquid level gauge 20 for externally checking the amount of the hydraulic oil accommodated in the hydraulic oil tank 10 is attached to a metal side surface 10a of the hydraulic oil tank 10. Since the liquid level gauge 20 is attached to the side surface 10a of the hydraulic oil tank 10, a user can easily visually check the amount of the hydraulic oil accommodated in the hydraulic oil tank 10. In addition, a liquid sensor 30 that measures a physical quantity (hue in the present embodiment) of liquid (hydraulic oil in the present embodiment) is attached to the outside of the liquid level gauge 20.

Figure 2:
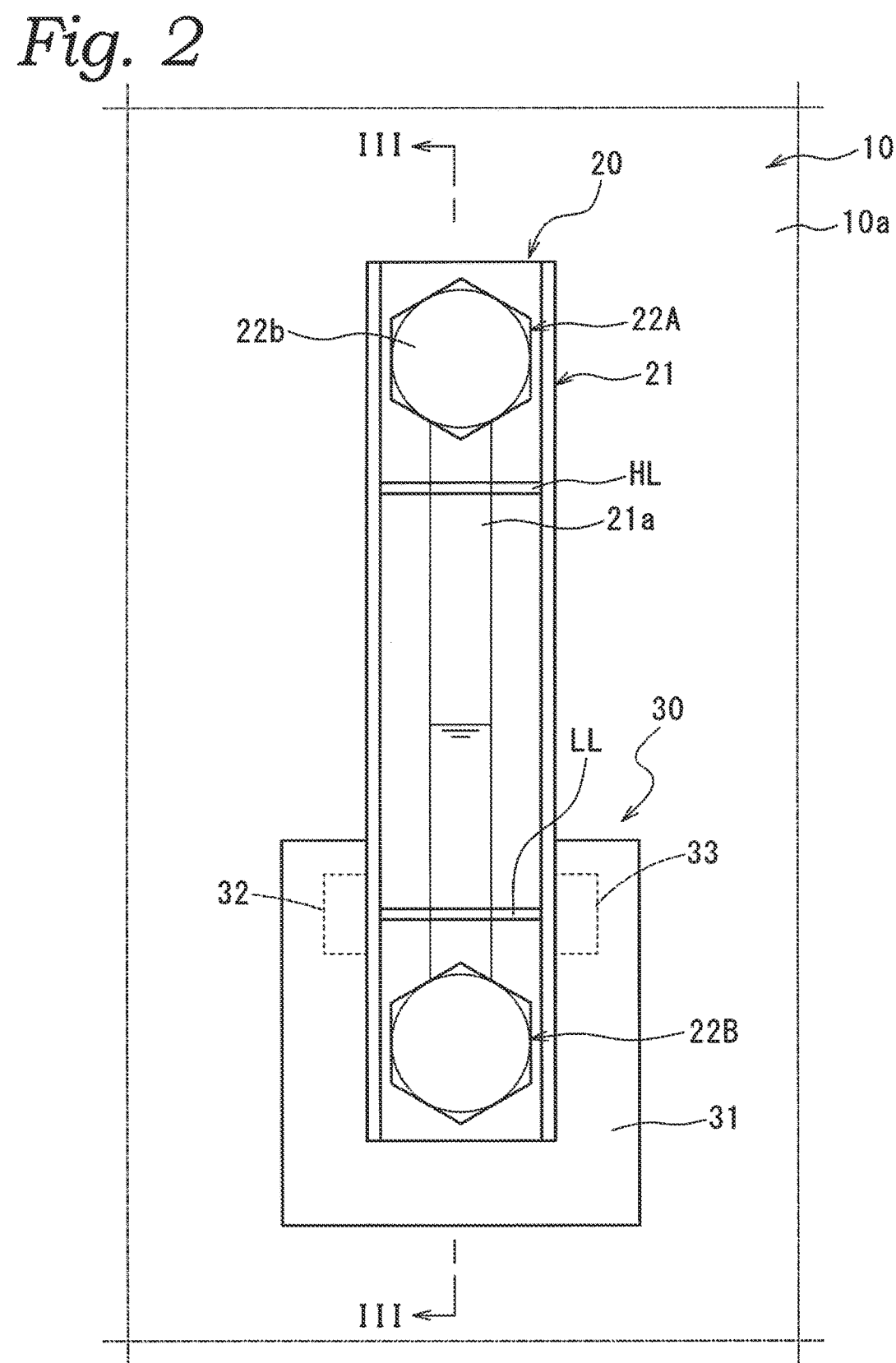
FIG. 2 is a front view of a liquid sensor according to the first embodiment.
Figure 3:
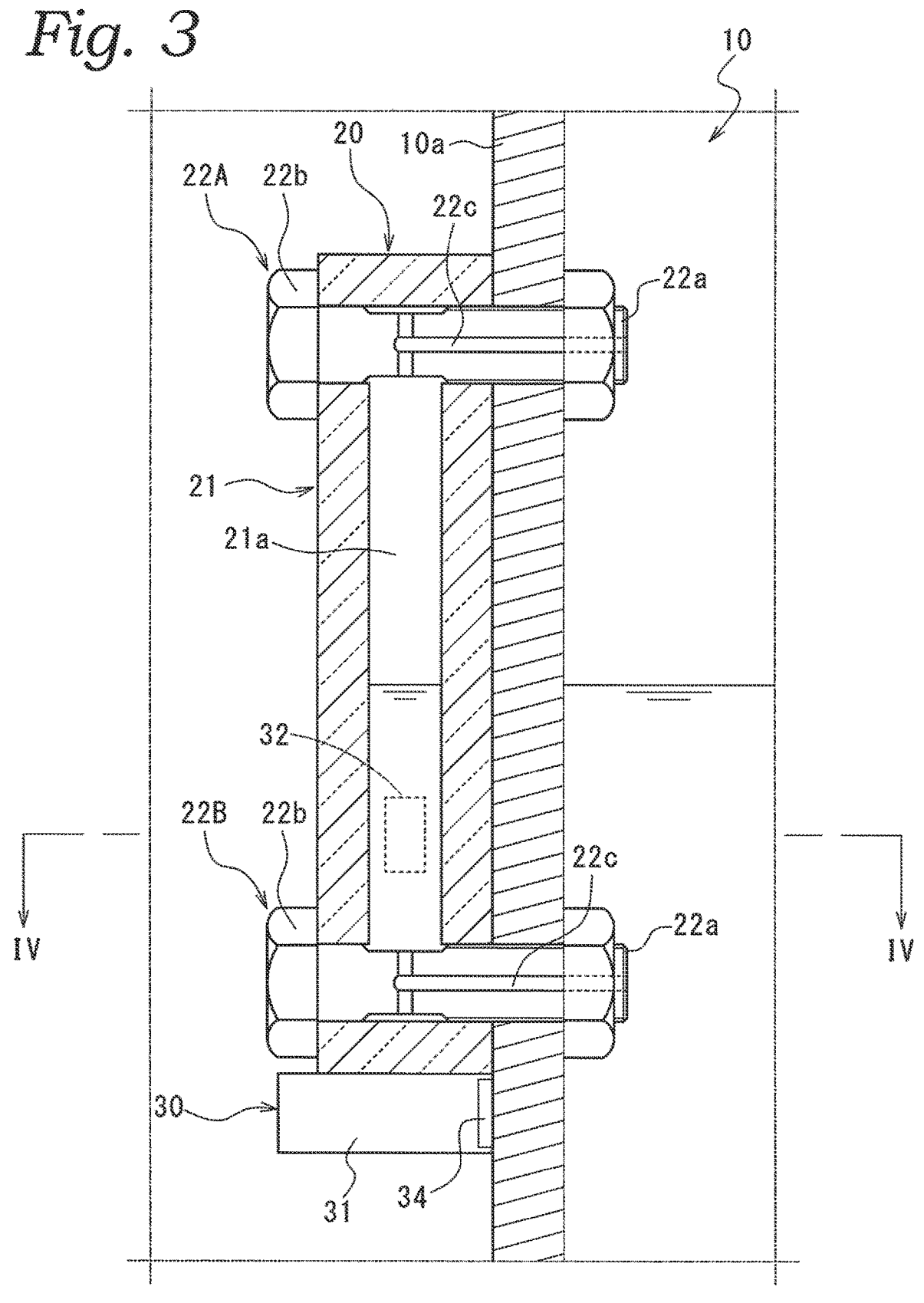
FIG. 3 is a cross-sectional view taken along line III-III in FIG. 2.

FIG. 2 is a schematic front view showing the liquid level gauge 20 and the liquid sensor 30 according to the present embodiment. FIG. 3 is a schematic cross-sectional view taken along line III-III in FIG. 2. In FIG. 3, illustration of a detailed structure of the inside of the liquid sensor 30 is omitted. In FIGS. 2 and 3, the same components as in FIG. 1 are denoted by the same reference signs as in FIG. 1.

Referring to FIGS. 2 and 3, the liquid level gauge 20 of the present embodiment is an oil level gauge for checking the oil level of the hydraulic oil accommodated in the hydraulic oil tank 10. The liquid level gauge 20 of the present embodiment includes a liquid level gauge main body 21 made of a transparent acrylic resin and two bolts 22A and 22B for fixing the liquid level gauge main body 21 to the hydraulic oil tank 10. The liquid level gauge 20 according to the present embodiment is an example of a translucent accommodation unit into which the liquid (hydraulic oil in the present embodiment) according to the present disclosure is introduced.

The liquid level gauge main body 21 of the present embodiment has a substantially rectangular parallelepiped shape, and is attached to the hydraulic oil tank 10 such that the liquid level gauge main body 21 has a longitudinal direction that extends along the vertical direction. The liquid level gauge main body 21 is hollow. Specifically, the liquid level gauge main body 21 includes a hollow portion 21*a* being a space extending in the longitudinal direction inside the liquid level gauge main body 21. The hydraulic oil is introduced into the hollow portion 21*a* of the liquid level gauge main body 21 according to the amount of the hydraulic oil accommodated in the hydraulic oil tank 10. The user can check the amount of the hydraulic oil accommodated in the hydraulic oil tank 10 by visually observing the oil level of the hydraulic oil in the hollow portion 21*a* of the liquid level gauge main body 21. The liquid level gauge main body 21 is provided with an upper limit line HL indicating the upper limit of an allowable range of the oil level of the hydraulic oil and a lower limit line LL indicating the lower limit of the allowable range of the oil level of the hydraulic oil.

The bolts 22A and 22B of the present embodiment are made of metal. As shown in FIG. 3, each of the bolts 22A and 22B includes a communication portion 22*c* extending in the axial direction from a tip portion 22*a* toward a head portion 22*b* of the bolt. The communication portion 22*c* is open in the radial direction at an axial end portions on the head portion 22*b* side of each of the bolts 22A and 22B. In other words, the bolts 22A and 22B are what are called perforated bolts. The communication portions 22*c* of the bolts 22A and 22B fluidly connect the internal space of the hydraulic oil tank 10 to the hollow portion 21*a* of the liquid level gauge main body 21 in a state where the bolts 22A and 22B fix the liquid level gauge main body 21 to the hydraulic oil tank 10. In other words, the internal space of the hydraulic oil tank 10, the hollow portion 21*a* of the liquid level gauge main body 21, and the communication portion 22*c* of the bolts 22A and 22B communicate with each other.

In the state shown in FIG. 3, the communication portion 22*c* of the bolt 22B opens at the tip portion 22*a* into an area where the hydraulic oil accumulated in the hydraulic oil tank 10 exists. At this time, the hydraulic oil is introduced from the hydraulic oil tank 10 into the hollow portion 21*a* of the liquid level gauge main body 21 through the communication portion 22*c* of the bolt 22B. In addition, the communication portion 22*c* of the bolt 22B is filled with hydraulic oil.

As shown in FIG. 3, the oil level of the hydraulic oil introduced into the liquid level gauge main body 21 coincides with the oil level of the hydraulic oil accommodated in the hydraulic oil tank 10. Thus, the user can check the amount of the hydraulic oil accommodated in the hydraulic oil tank 10 by visually observing the oil level of the hydraulic oil in the hollow portion 21*a* of the liquid level gauge main body 21.

The liquid sensor 30 of the present embodiment is a photoelectric sensor for detecting the degree of deterioration of the hydraulic oil accommodated in the hydraulic oil tank 10 and the presence or absence of the hydraulic oil. More specifically, the liquid sensor 30 is a transmissive color sensor. As shown in FIG. 2, the liquid sensor 30 of the present embodiment includes a U-shaped casing 31, a light emitter 32 that emits light, and a light receiver 33 that receives the light emitted from the light emitter 32. The light emitter 32 and the light receiver 33 are provided integrally with the casing 31 so as to face each other. Specifically, the light emitter 32 and the light receiver 33 are provided integrally with the casing 31 so that the optical axis of the light emitter 32 and the optical axis of the light receiver 33 coincide with each other.

The liquid sensor 30 is attached to the liquid level gauge main body 21 such that the light emitter 32 and the light receiver 33 face each other across the liquid level gauge main body 21. In addition, the liquid sensor 30 is attached to the liquid level gauge 20 such that the height positions of the light emitter 32 and the light receiver 33 overlap with the height position of the lower limit line LL of the liquid level gauge main body 21. The liquid sensor 30 detects the presence or absence of hydraulic oil below the lower limit line LL of the liquid level gauge main body 21.

A packing (not shown) is provided between the casing 31 of the liquid sensor 30 and the liquid level gauge main body 21 of the present embodiment. This packing makes the casing 31 and the liquid level gauge main body 21 water-resistant and dust-resistant, prevents external light from entering the liquid level gauge main body 21, and brings the casing 31 into close contact with the liquid level gauge main body 21 so that the casing 31 is held by the liquid level gauge main body 21.

The light emitter 32 of the present embodiment includes a light emitting element for emitting light and a drive circuit for driving the light emitting element. The light emitting element of the present embodiment is a white light emitting diode. In other words, the light emitter 32 of the present embodiment emits white light.

The light receiver 33 of the present embodiment includes a light receiving element that converts the intensity of light into an electric signal, an amplifier circuit that amplifies the electric signal output from the light receiving element, and an A/D conversion circuit that converts the analog electric signal amplified by the amplifier circuit into a digital electric signal. The light receiving element of the present embodiment is an RGB color sensor, and can detect the electric signal converted from received visible light separately for each color of red, green, and blue.

As shown in FIG. 3, the liquid sensor 30 of the present embodiment further includes a thermoelectric conversion element 34 that converts heat into electric power. The thermoelectric conversion element 34 of the present embodiment is provided so as to be in contact with the side surface 10*a* of the hydraulic oil tank 10. The side surface 10*a* of the hydraulic oil tank 10 is likely to have a high temperature because the hydraulic oil accommodated in the hydraulic oil tank 10 has a high temperature due to heat generation from a sliding portion of the machine tool or the like. The thermoelectric conversion element 34 generates power using a temperature difference between the temperature of the side surface 10*a* of the hydraulic oil tank 10 and the temperature of the air around the liquid sensor 30.

Figure 4:
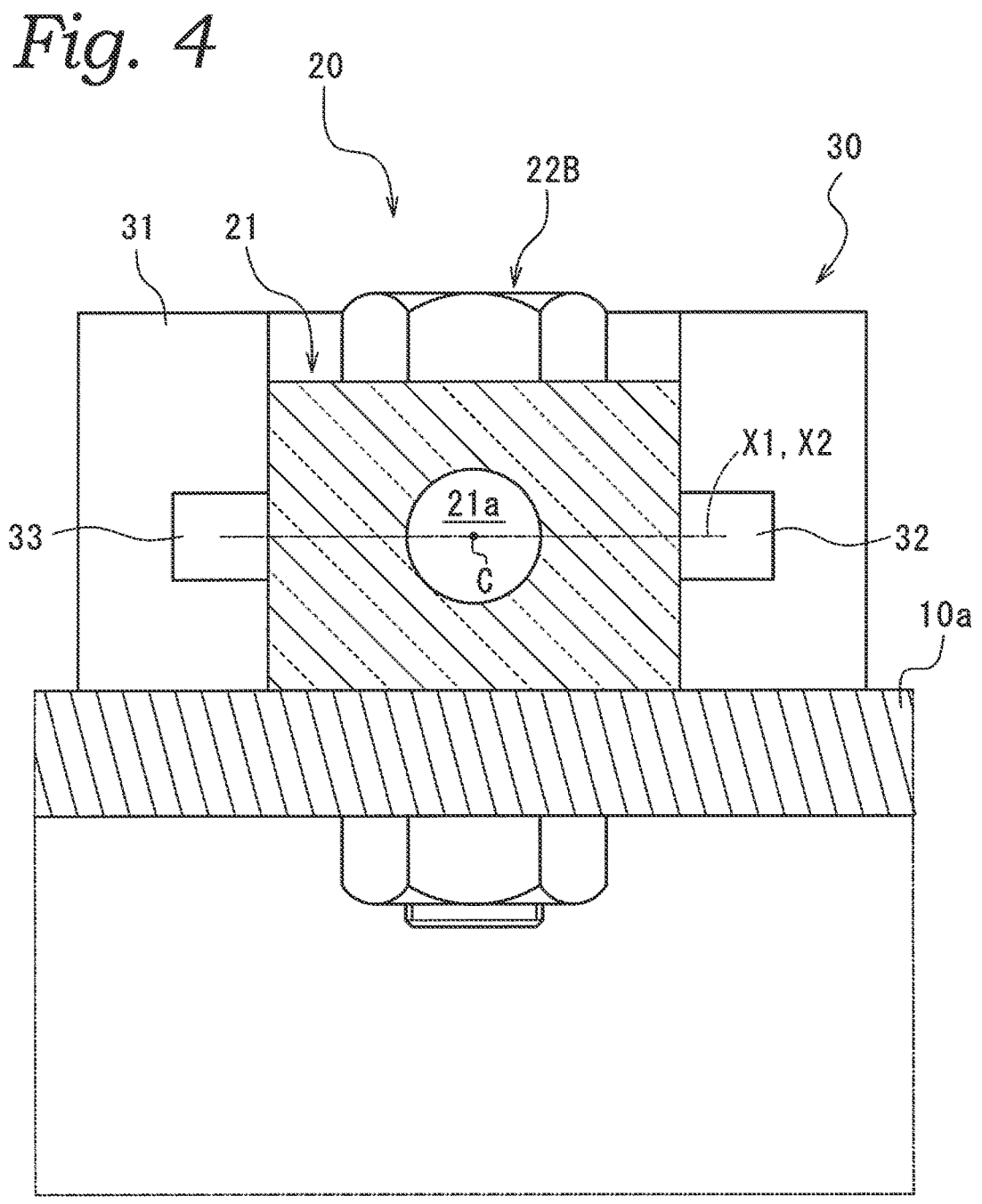
FIG. 4 is a cross-sectional view taken along line IV-IV in FIG. 3.

FIG. 4 is a schematic cross-sectional view taken along line IV-IV in FIG. 3. In FIG. 4, illustration of a detailed structure of the inside of the liquid sensor 30 is omitted. In FIG. 4, the same components as in FIG. 1 to 3 are denoted by the same reference signs as in FIGS. 1 to 3.

Referring to FIG. 4, the hollow portion 21*a* of the liquid level gauge main body 21 has a circular cross-sectional shape in the cross section shown in FIG. 4.

As shown in FIG. 4, the optical axis X1 of the light emitter 32 and the optical axis X2 of the light receiver 33 coincide with each other. In addition, the optical axis X1 of the light emitter 32 and the optical axis X2 of the light receiver 33 extend to pass through the center C of the hollow portion 21*a* of the liquid level gauge main body 21. Here, the optical axis X1 of the light emitter 32 and the optical axis X2 of the light receiver 33 do not necessarily need to pass through the center C of the hollow portion 21*a*. It is preferable that the shortest distance from the optical axis X1 of the light emitter 32 and the optical axis X2 of the light receiver 33 to the center C of the hollow portion 21*a* is 5 mm or less.

Figure 5:
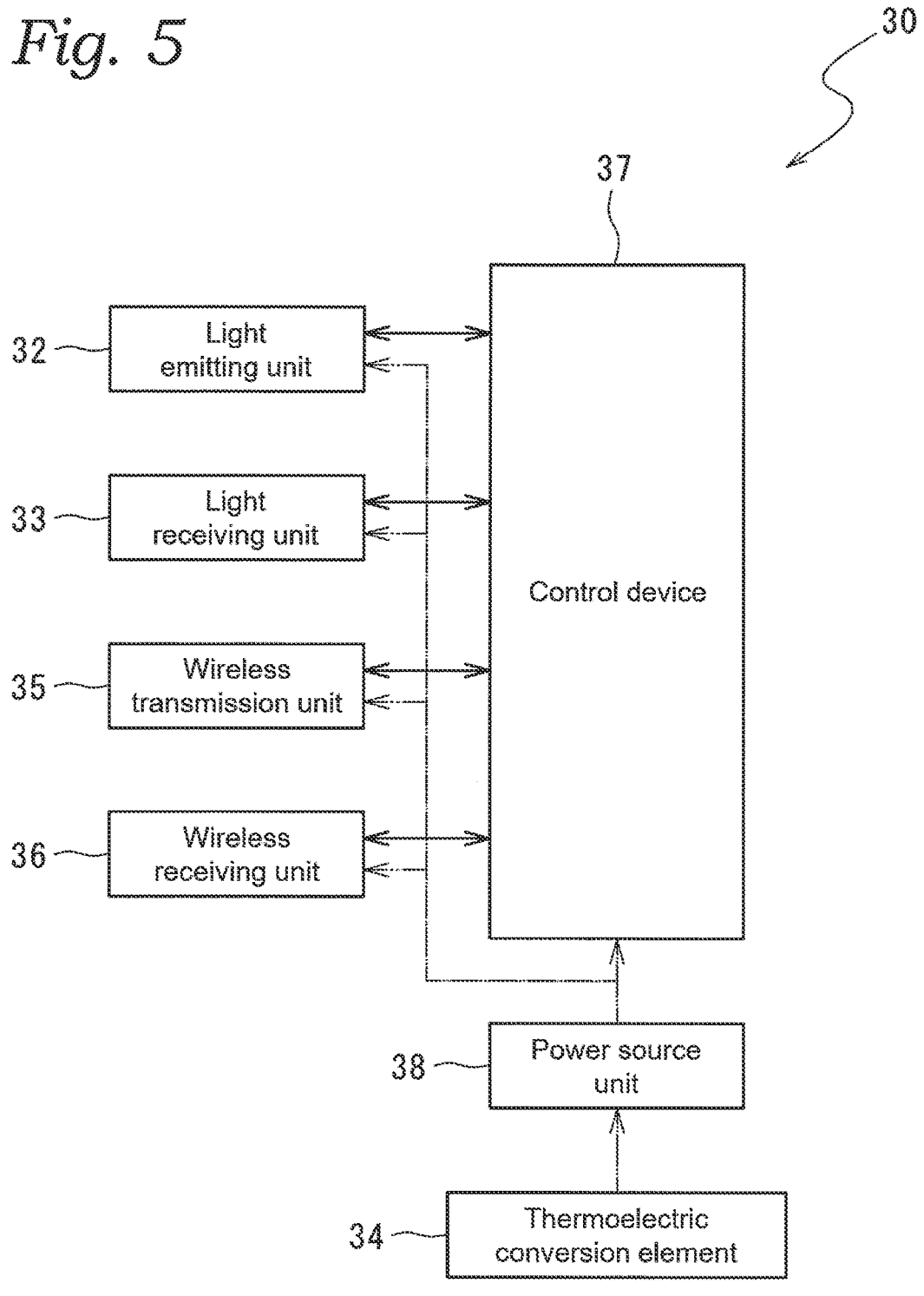
FIG. 5 is a block diagram of the liquid sensor according to the first embodiment.

FIG. 5 is a block diagram of the liquid sensor 30 of the present embodiment. In FIG. 5, the same components as in FIGS. 1 to 3 are denoted by the same reference signs as in FIGS. 1 to 3.

Referring to FIG. 5, the liquid sensor 30 of the present embodiment includes a wireless transmitter 35 that wirelessly transmits a signal to an external apparatus, a wireless receiver 36 that wirelessly receives a signal from an external apparatus, and a control device 37.

The wireless transmitter 35 communicates with the controller 13 (shown in FIG. 1) of the hydraulic unit 1, and transmits an electric signal output from the light receiver 33 to the controller 13 of the hydraulic unit 1. The wireless receiver 36 communicates with the controller 13 of the hydraulic unit 1, and receives an electric signal such as a control signal from the controller 13 of the hydraulic unit 1. The control device 37 controls the light emitter 32, the light receiver 33, the wireless transmitter 35, and the wireless receiver 36.

The liquid sensor 30 further includes a power source 38 for supplying (see a two-dot chain line in FIG. 5) power to each of the light emitter 32, the light receiver 33, the wireless transmitter 35, the wireless receiver 36, and the control device 37. The power source 38 of the present embodiment includes a rechargeable battery. In addition, the power source 38 is electrically connected to the thermoelectric conversion element 34. The thermoelectric conversion element 34 generates electric power for charging the power source 38 using a temperature difference between the hydraulic oil tank 10 (shown in FIG. 1) and air around the liquid sensor 30.

(Measurement Using Liquid Sensor)

The light emitter 32 of the liquid sensor 30 according to the present embodiment emits white light from the light emitting element with the power supplied from the power source 38. The light receiver 33 of the liquid sensor 30 receives light emitted from the light emitter 32 and having passed through the liquid level gauge main body 21 and the hydraulic oil in the liquid level gauge main body 21. The liquid sensor 30 transmits the light intensity of each of colors of red, green, and blue of light received by the light receiving element of the light receiver 33 to the controller 13 (shown in FIG. 1) of the hydraulic unit 1 via the wireless transmitter 35 as an electric signal. Since each of the red, green, and blue lights received by the light receiver 33 is light having a wavelength that was not absorbed by the hydraulic oil in the level gauge 20, it is possible to detect the hue of the hydraulic oil in the liquid level gauge 20 from the intensity of those lights transmitted by the light sensor 30. In other words, the light receiver 33 of the liquid sensor 30 according to the present embodiment converts the hue being an example of the physical quantity of the hydraulic oil into an electric signal and outputs the electric signal. In short, the liquid sensor 30 according to the present disclosure outputs a signal related to a physical quantity (hue in the present embodiment) of liquid (hydraulic oil in the present embodiment). Here, the translucency of the liquid level gauge 20 according to the present disclosure is translucency with respect to light (white light in the present embodiment) emitted by the light emitter 32.

The controller 13 (shown in FIG. 1) of the hydraulic unit 1 of the present embodiment determines the degree of deterioration of the hydraulic oil and the presence or absence of the hydraulic oil based on the signal related to the hue of the hydraulic oil output from the liquid sensor 30. In other words, the liquid sensor 30 of the present embodiment outputs a signal related to the degree of deterioration of the hydraulic oil and a signal related to the presence or absence of the hydraulic oil. The degree of deterioration of the hydraulic oil and the presence or absence of the hydraulic oil are examples of physical quantities of the liquid (hydraulic oil in the present embodiment) according to the present disclosure.

Figure 6:
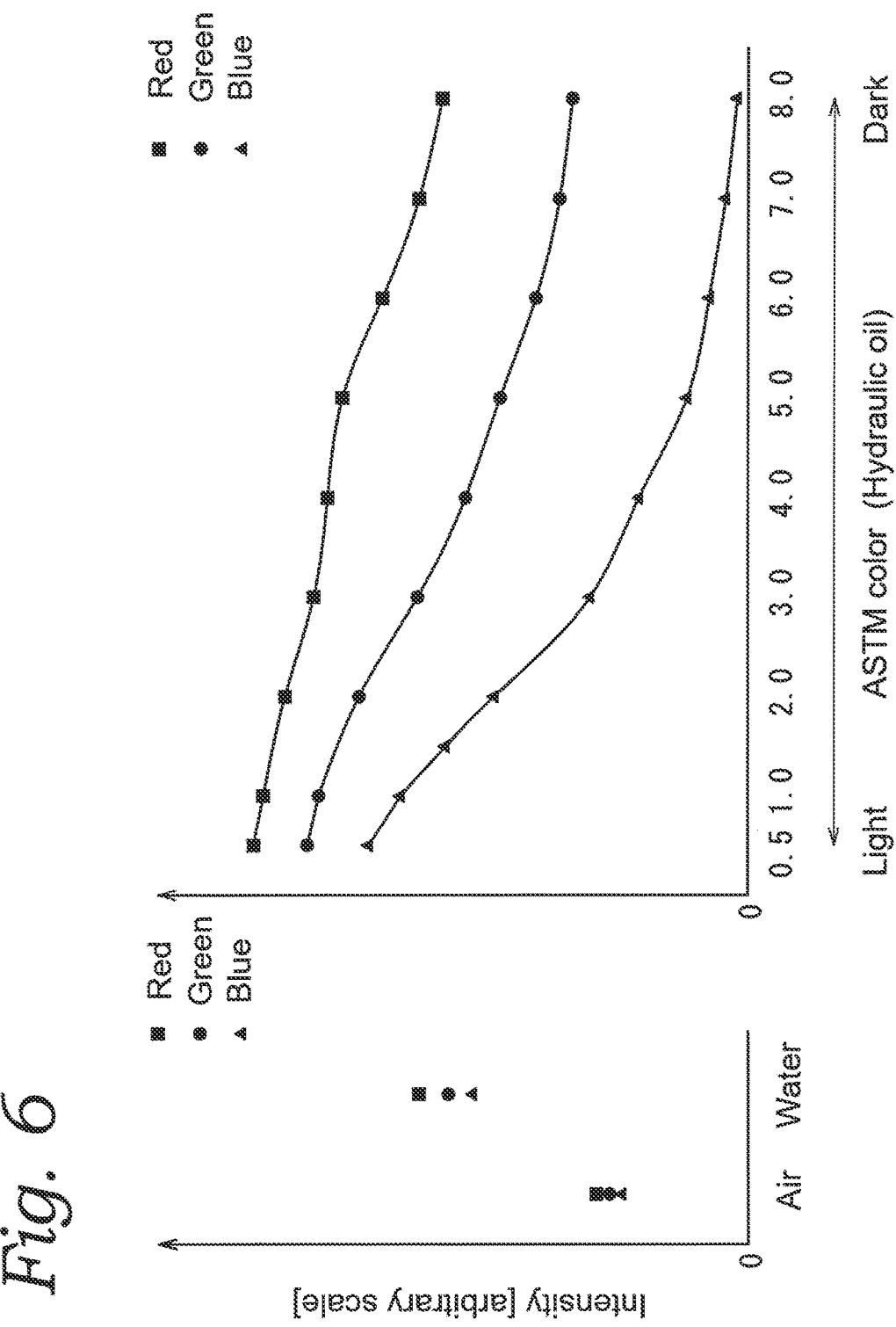
FIG. 6 is a graph relating to a hue detected by the liquid sensor according to the first embodiment.

FIG. 6 is an example of a calibration curve related to the hue used to determine the degree of deterioration of the hydraulic oil and the presence or absence of the hydraulic oil in the present embodiment. FIG. 6 shows the intensity [arbitrary scale] of light for each color of red, green, and blue for air, water, and the hydraulic oil having different hues. In the present embodiment, the hue of the hydraulic oil is represented using an ASTM color measured conforming to ASTM D1500. The ASTM color numerically indicates the hue of the hydraulic oil by a color scale ranging from 0.5 of a light color to 8.0 of a dark color in increments of 0.5. The ASTM color is an index of the degree of deterioration of the hydraulic oil, and indicates that the larger the value of the ASTM color, the more the hydraulic oil is deteriorated. In the present embodiment, the calibration curve (or calibration table) as shown in FIG. 6 is stored in the controller 13 (shown in FIG. 1) of the hydraulic unit 1.

In the present embodiment, the controller 13 (shown in FIG. 1) of the hydraulic unit 1 determines the degree of deterioration of the hydraulic oil and the presence or absence of the hydraulic oil using the electric signals for each color of the red, green, and blue output from the liquid sensor 30 and the calibration curve shown in FIG. 6. Specifically, the controller 13 of the hydraulic unit 1 compares the intensity (hereinafter, referred to as a measurement result of the liquid sensor 30) of light for each color of red, green, and blue for the hydraulic oil to be measured, which are calculated from the output voltage of the light receiver 33 of the liquid sensor 30, with the calibration curve shown in FIG. 6. The degree of deterioration of the hydraulic oil is calculated from the measurement result of the liquid sensor 30 using the calibration curve for the ASTM color in FIG. 6. In addition, the presence or absence of the hydraulic oil is determined based on whether or not the measurement result of the liquid sensor 30 indicates air by comparing the measurement result of the liquid sensor 30 with the calibration curve in FIG. 6. If determining that the measurement result of the liquid sensor 30 indicates air, the controller 13 of the hydraulic unit 1 determines that there is no hydraulic oil at the detection position (in the present embodiment, below the lower limit line LL) of the liquid sensor 30.

When the temperature in a factory where the hydraulic unit 1 is installed is low, dew condensation occurs on the inner surface of the liquid level gauge main body 21 that defines the hollow portion 21a, and the liquid sensor 30 may make an erroneous determination due to irregular reflection caused by the dew condensation or moisture mixing into the hydraulic oil. Therefore, the measurement using the liquid sensor 30 described above is preferably performed after it is determined that the hydraulic unit 1 is in a stable operation state by referring to the operation time or the oil temperature rise after the start of the hydraulic unit 1.

(Notification by Liquid Sensor)

The liquid sensor 30 notifies the user of information on the physical quantity of the liquid (for example, abnormality) based on the light emission manner of the light emitter 32. Specifically, the liquid sensor 30 notifies the user of the abnormalities related to the deterioration degree of the hydraulic oil and the presence or absence of the hydraulic oil based on the light emission manner of the light emitter 32.

In the present embodiment, when the controller 13 (shown in FIG. 1) of the hydraulic unit 1 determines that the hydraulic oil has deteriorated more than the predetermined deterioration degree, or determines that there is no hydraulic oil at the detection position, the controller 13 of the hydraulic unit 1 transmits a control signal for controlling the light emitter 32 to the liquid sensor 30. When the wireless receiver 36 of the liquid sensor 30 receives the control signal from the controller 13 of the hydraulic unit 1, the control device 37 controls the light emitter 32 so that the light emission manner of the light emitter 32 changes according to contents to be notified. Thus, the liquid sensor 30 notifies the user of the abnormality (deterioration in hydraulic oil or decrease in hydraulic oil amount). The predetermined deterioration degree is, for example, a deterioration degree when the ASTM color becomes dark to 2.5 or more.

The light emission manner of the light emitter 32 is determined according to contents to be notified (in the present embodiment, deterioration of hydraulic oil and decrease in hydraulic oil amount). In other words, in the light emitter 32 of the present embodiment, the light emission manner is determined according to the signal related to the physical quantity of the hydraulic oil. When the deterioration of the hydraulic oil is notified, the light emitter 32 of the present embodiment blinks. In other words, when the deterioration of the hydraulic oil is notified, the light emission manner of the light emitter 32 changes from off to blinking. In addition, when the decrease in the hydraulic oil amount is notified, the light emitter 32 of the present embodiment is turned on. In other words, when the decrease in the hydraulic oil amount is notified, the light emission manner of the light emitter 32 changes from off to on. For example, the light emission manner of the light emitter 32 may change a blinking pattern such as a blinking interval and a blinking speed according to contents to be notified.

The controller 13 (shown in FIG. 1) of the hydraulic unit 1 may display a numerical value (for example, ASTM color value) or a color in accordance with the level of the deterioration degree of the hydraulic oil on a display unit 13*a* provided in the controller 13, a display unit (not shown) provided in an external apparatus to which the hydraulic unit 1 supplies the hydraulic oil, or the like. Thus, it is possible to alert the user to replace the hydraulic oil before the hydraulic oil needs to be replaced.

In addition, the controller 13 (shown in FIG. 1) of the hydraulic unit 1 may notify the user of deterioration of the hydraulic oil before the hydraulic oil needs to be replaced. For example, the controller 13 of the hydraulic unit 1 may notify the user of the deterioration of the hydraulic oil by causing the light emitter 32 to emit light even before the ASTM color becomes dark to 2.5 or more, for example. In this case, as the deterioration of the hydraulic oil progresses, the frequency of light emission of the light emitter 32 may increase.

According to the liquid sensor 30 of the present disclosure, since the light emitter 32 and the light receiver 33 are attached to the outside of the liquid level gauge 20 into which the hydraulic oil to be measured is introduced, a seal structure for preventing leakage of the hydraulic oil introduced into the liquid level gauge 20 to the outside is not required between the liquid sensor 30 and the liquid level gauge 20, and workability of attachment work of the liquid sensor 30 to the liquid level gauge 20 can be improved.

In general, in the transmission type sensor, the surface of the liquid level gauge 20 has less influence on the detection accuracy than in other types of photoelectric sensors. In the above embodiment, since the liquid sensor 30 is a transmission type sensor, it is possible to perform reliable detection as compared with a case where a sensor of another type is used as the liquid sensor 30.

In the above embodiment, since the light emitter 32 and the light receiver 33 are integrally provided in the casing 31 in a state where the optical axis of the light emitter 32 and the optical axis of the light receiver 33 are made to coincide with each other, it is not necessary to adjust the optical axes of the light emitter and the light receiver when the liquid sensor 30 is attached, so that workability of attachment work of the liquid sensor 30 to the liquid level gauge 20 can be improved.

According to the liquid sensor 30 of the present disclosure, since the liquid sensor 30 includes the rechargeable power source 38 that supplies power to the light emitter 32 and the light receiver 33 and the thermoelectric conversion element 34 that generates power for charging the power source 38, wiring for supplying power from the outside to the liquid sensor 30 is not required, and the wiring structure can be simplified.

According to the above embodiment, since the detection result of the liquid sensor 30 is transmitted to the controller 13 of the hydraulic unit 1 via the wireless transmitter 35, there is no need for wiring for outputting the signal output from the light receiver 33 to the outside, and the wiring structure can be simplified.

In the above embodiment, the liquid sensor 30 notifies the user of information on the physical quantity of the hydraulic oil by the light emission manner of the light emitter 32. For example, when the detection result of the liquid sensor 30 indicates an abnormality, the light emitter 32 of the liquid sensor 30 emits light in a light emission manner corresponding to the abnormality, whereby the liquid sensor 30 notifies the user that the liquid sensor 30 has detected the abnormality. Thus, the user can easily recognize the information (for example, abnormality) on the physical quantity of the hydraulic oil by visually observing the light emission manner of the liquid sensor 30.

In addition, since the light emitter 32 of the liquid sensor 30 has both a function as a projector of a photoelectric sensor and a function of notifying the user according to the signal related to the physical quantity of the hydraulic oil, the structure of the liquid sensor 30 can be simplified as compared with a case where these functions are separately provided.

In general, a liquid level gauge is installed at a place where a user can easily visually observe. Therefore, according to the above embodiment, since the liquid sensor 30 is attached to the liquid level gauge, the user can easily visually observe the light emitter 32 of the liquid sensor 30, so that the user can easily recognize the information (for example, abnormality) on the physical quantity of the liquid to be measured.

In the present embodiment, the controller 13 of the hydraulic unit 1 determines the degree of deterioration of the hydraulic oil and the presence or absence of the hydraulic oil. However, the control device 37 of the liquid sensor 30 may determine the degree of deterioration of the hydraulic oil and the presence or absence of the hydraulic oil. In this case, the liquid sensor 30 does not need to include the wireless transmitter 35 and the wireless receiver 36.

Second Embodiment

A liquid level gauge 120 of the second embodiment has the same configuration as the liquid level gauge 20 of the first embodiment except for including a float 123, and the description of the first embodiment referring to FIGS. 1 and 5 is applied to the second embodiment. In the second embodiment, components similar to those of the first embodiment are denoted by the identical reference signs, and the detailed description thereof will be omitted.

Figure 7:
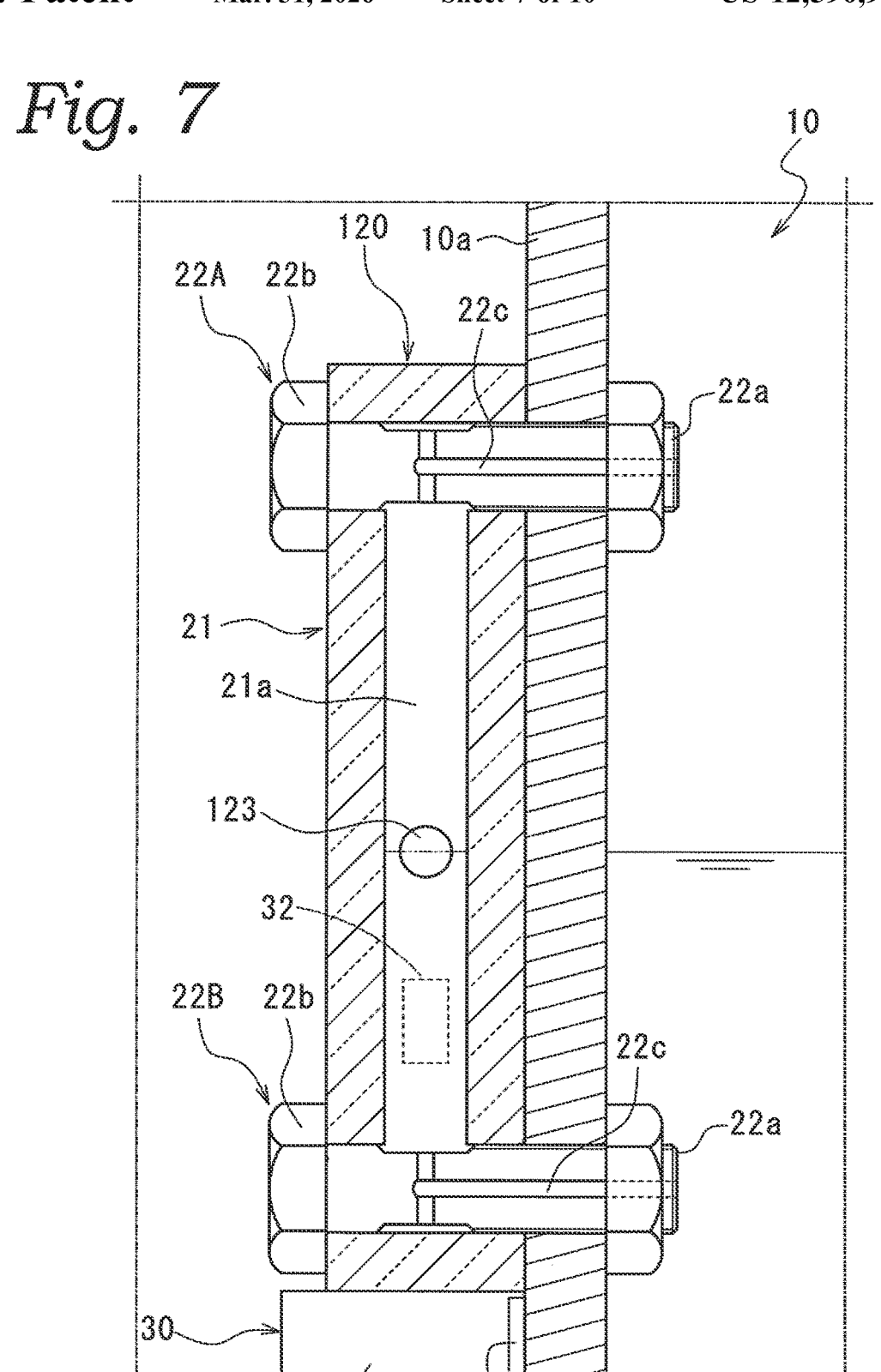
FIG. 7 is a cross-sectional view similar to FIG. 3 according to a second embodiment of the present disclosure.

FIG. 7 is a schematic cross-sectional view similar to FIG. 3 of the liquid level gauge 120 and the liquid sensor 30 of a third embodiment.

Referring to FIG. 7, the liquid level gauge 120 of the second embodiment includes a float 123 disposed in the hollow portion 21a of the liquid level gauge main body 21. The float 123 is configured to float on the hydraulic oil. Thus, the float 123 indicates the position of the oil level of the hydraulic oil. The float 123 is made of a material having low transmittance with respect to the light emitted from the light emitter 32 so as to block the light emitted from the light emitter 32.

The second embodiment produces actions and effects similar to those of the first embodiment.

In addition, according to the second embodiment, when the float 123 is at a level at which the light emitter 32 and the light receiver 33 are attached to the liquid level gauge 120, the float 123 blocks the light emitted from the light emitter 32 and significantly changes the intensity of the light received by the light receiver 33, it is possible to improve the accuracy of detecting the presence or absence of the hydraulic oil.

Third Embodiment

A liquid sensor 230 of the third embodiment has the same configuration as the liquid sensor 30 of the first embodiment except for the configuration of a thermoelectric conversion element 234, and the description of the first embodiment referring to FIGS. 1 and 5 is applied to the third embodiment. In the third embodiment, components similar to those of the first embodiment are denoted by the identical reference signs, and the detailed description thereof will be omitted.

Figure 8:
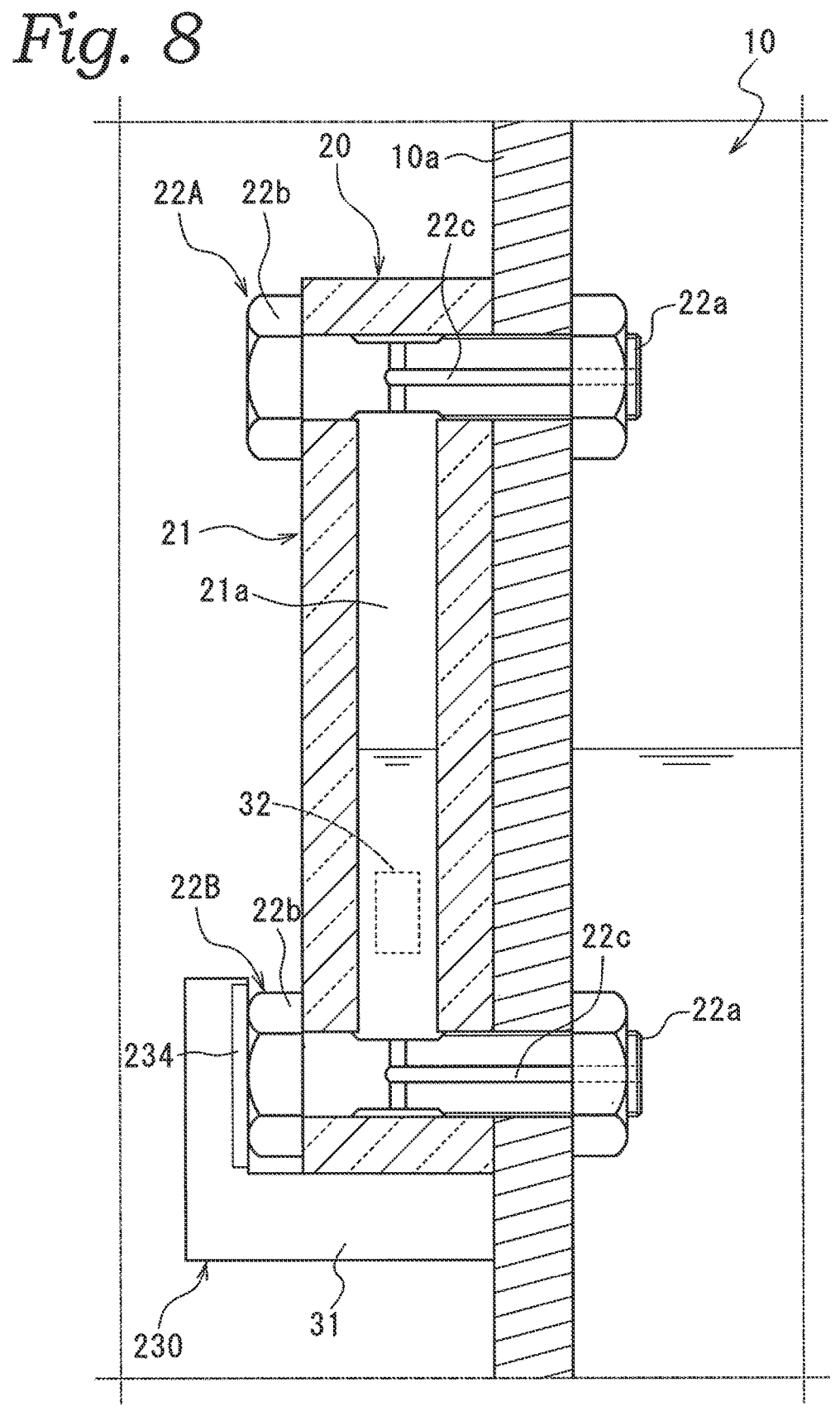

FIG. 8 is a schematic cross-sectional view similar to FIG. 3 of the liquid level gauge 20 and the liquid sensor 230 of the third embodiment.

Referring to FIG. 8, the thermoelectric conversion element 234 of the present embodiment is provided so as to be in contact with the head portion 22b of the bolt 22B.

The third embodiment produces actions and effects similar to those of the first embodiment.

In addition, since the communication portion 22c of the bolt 22B is filled with the hydraulic oil, the head portion 22b of the bolt 22B made of metal tends to reach a high temperature by the heat of the hydraulic oil. According to the third embodiment, since the thermoelectric conversion element 234 is provided to be in contact with the head portion 22b of the metal bolt 22B, the thermoelectric conversion element 234 can effectively generate electric power.

Fourth Embodiment

A liquid sensor 30 of the fourth embodiment has the same configuration as the liquid sensor 30 of the first embodiment except for the configuration of the light emitter 32 and the light receiver 33, and the description of the first embodiment referring to FIGS. 1 and 5 is applied to the fourth embodiment. In the fourth embodiment, components similar to those of the first embodiment are denoted by the identical reference signs, and the detailed description thereof will be omitted.

The light emitter 32 of the present embodiment includes a red light emitting diode, a green light emitting diode, and a blue light emitting diode. The light emitter 32 of the present embodiment can change the emission color by adjusting the amount of light emission of each of the red light emitting diode, the green light emitting diode, and the blue light emitting diode.

The light emission manner of the light emitter 32 is determined according to contents to be notified (in the present embodiment, deterioration of hydraulic oil and decrease in hydraulic oil amount). In the light emitter 32 of the present embodiment, the emission color changes according to the signal related to the physical quantity of the hydraulic oil. When the deterioration of the hydraulic oil is notified, the light emitter 32 of the present embodiment alternately changes the emission color to, for example, green and red. In addition, when the decrease in the hydraulic oil amount is notified, the light emitter 32 of the present embodiment alternately changes the emission color to, for example, blue and red.

The fourth embodiment produces actions and effects similar to those of the first embodiment.

Fifth Embodiment

Figure 9:
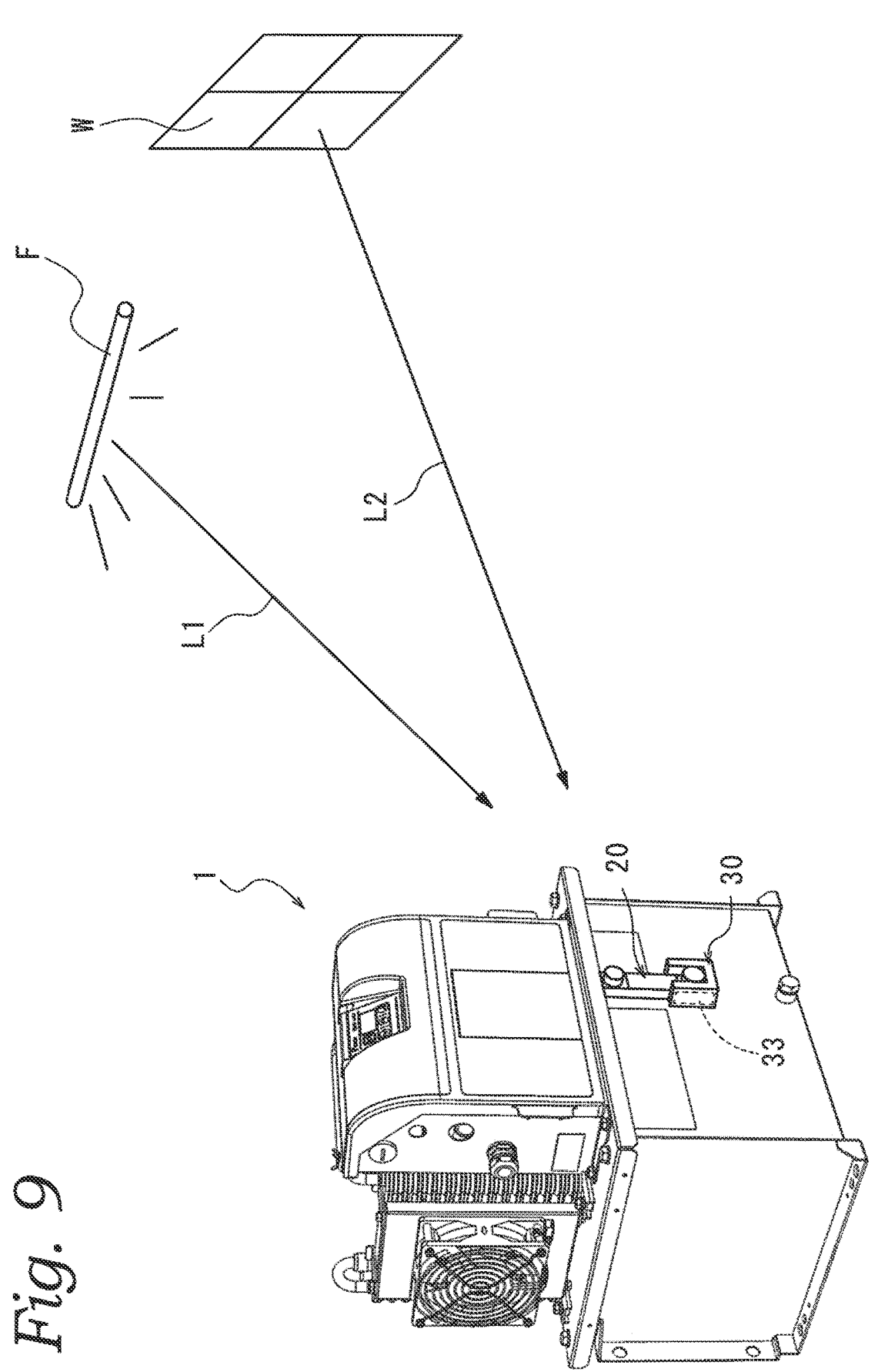
FIG. 9 is a schematic perspective view of a hydraulic unit according to a fifth embodiment of the present disclosure.

A liquid sensor 30 of the fifth embodiment has the same configuration as the liquid sensor 30 of the first embodiment except for not including the light emitter 32, and a detailed description thereof will be omitted. FIG. 9 is a schematic diagram showing a state in which the hydraulic unit 1 according to the present embodiment is disposed in a factory.

Referring to FIG. 9, the light receiver 33 of the present embodiment may receive, for example, light L1 from a fluorescent lamp F in the factory where the hydraulic unit 1 is installed, which passes through the hydraulic oil introduced into the liquid level gauge 20. Alternatively, the light receiver 33 of the present embodiment may receive, for example, light L2 shining into the factory through a window W of the factory where the hydraulic unit 1 is installed, which passes through the hydraulic oil in the liquid level gauge 20. In this case, the liquid sensor 30 is preferably configured such that the casing 31 has translucency, or configured in an L shape by eliminating a portion facing the light receiver 33.

The fifth embodiment produces actions and effects similar to those of the first embodiment.

In addition, according to the fifth embodiment, since it is not necessary to provide the light emitter, the configuration of the liquid sensor 30 can be simplified.

Sixth Embodiment

Figure 10:
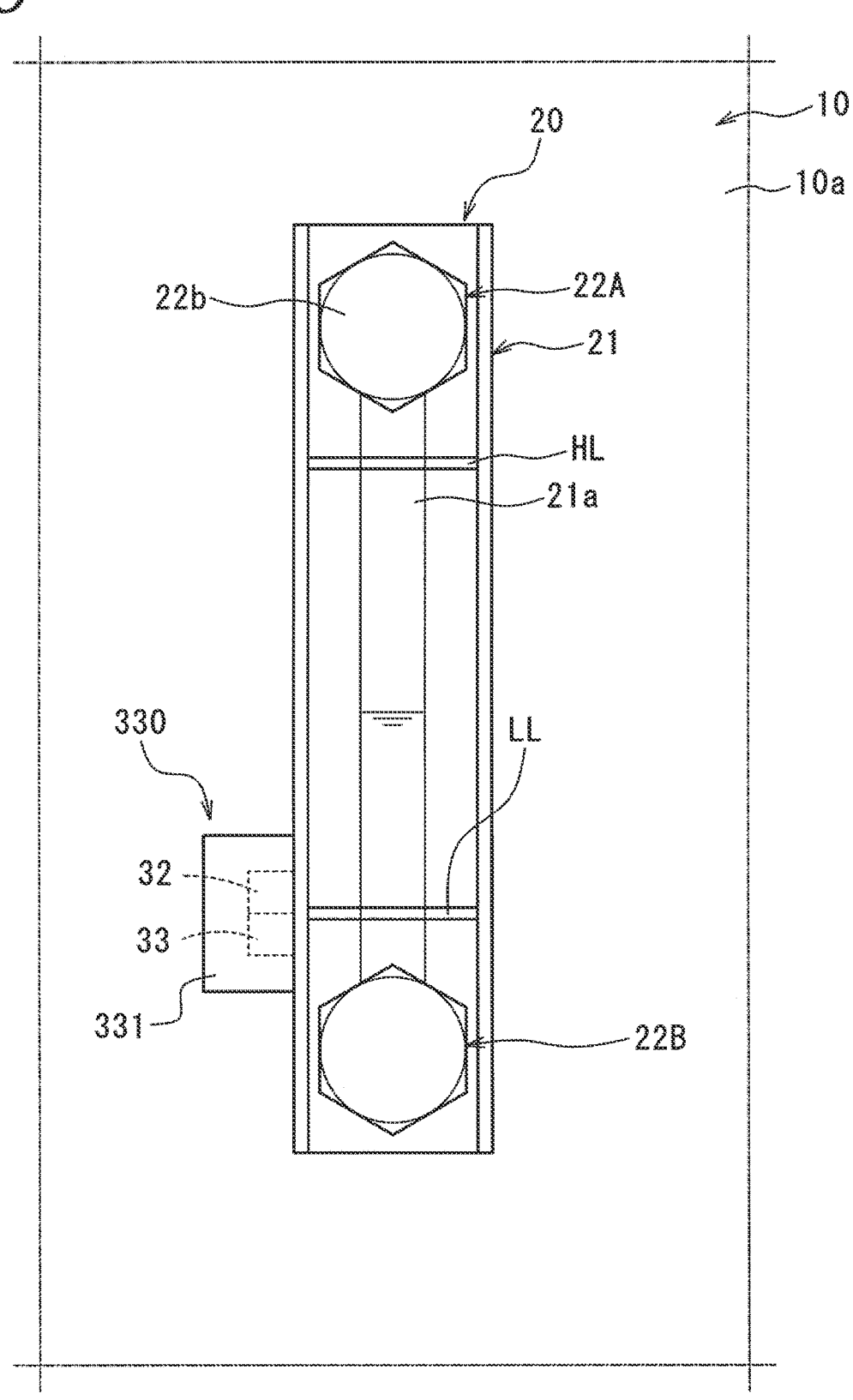
FIG. 10 is a perspective view of a hydraulic unit according to a sixth embodiment of the present disclosure.

A liquid sensor 330 of the sixth embodiment has the same configuration as the liquid sensor 30 of the first embodiment except for being a reflective sensor, and detailed description of the same configuration will be omitted. FIG. 10 is a schematic front view showing the liquid level gauge 20 and the liquid sensor 330 according to the present embodiment.

The liquid sensor 330 of the present embodiment is a reflective color sensor. As shown in FIG. 10, the liquid sensor 330 of the present embodiment includes a casing 331, a light emitter 32 that emits light, and a light receiver 33 that receives light emitted from the light emitter 32, passing through a liquid level gauge main body 21 having translucency, and reflected by the hydraulic oil in the liquid level gauge main body 21. In the present embodiment, the light emitter 32 and the light receiver 33 arc disposed on the same side with respect to the liquid level gauge main body 21.

The sixth embodiment produces actions and effects similar to those of the first embodiment.

According to the liquid sensor 330, since the light emitter 32 and the light receiver 33 are arranged on the same side with respect to the liquid level gauge main body 21, the liquid sensor 330 can be miniaturized as compared with a case where the light emitter and the light receiver are arranged across the liquid level gauge main body 21.

In addition, since the liquid sensor 330 is a reflective sensor, it is not necessary to adjust the optical axis of the light emitter 32 and the optical axis of the light receiver 33, and it is possible to easily attach the liquid sensor 330 to the liquid level gauge 20.

Although the embodiments have been described above, it will be understood that various changes in form and details can be made without departing from the spirit and scope of the claims.

For example, in the first to sixth embodiments, the measurement target of the liquid sensor 30 is the hydraulic oil of the hydraulic unit 1, but the measurement target of the liquid sensor 30 is not limited thereto, and another liquid such as cutting fluid or coolant liquid may be the measurement target. In other words, in the first to sixth embodiments, the liquid according to the present disclosure is hydraulic oil, but is not limited thereto, and may be other liquid such as cutting fluid, coolant liquid, or water.

In the first to sixth embodiments, the liquid sensor 30 is attached to the hydraulic unit 1, but t the liquid sensor 30 may be attached to another machine or apparatus.

In the first to sixth embodiments, the liquid sensor 30 or 230 is attached to the liquid level gauge 20, but the place where the liquid sensor is to be attached is not limited thereto, and the liquid sensor 30 or 230 has only to be attached to an object into which liquid is introduced and which has translucency.

In the first to sixth embodiments, the light emitter 32 and the light receiver 33 are provided integrally with the casing 31, but the light emitter 32 and the light receiver 33 may be separately provided.

The light emitting element of the liquid sensor 30 may be a monochromatic light source of red, green, blue, or another color.

In the first to sixth embodiments, the deterioration of the liquid (hydraulic oil in the embodiment) is determined based on the intensity of light of each color of red, green, and blue output from the liquid sensor, but the way of determining the deterioration of the liquid is not limited thereto. For example, electric signals for red, green, and blue colors output from the liquid sensor may be respectively converted into cyan, yellow, and magenta colors to be used for determination of deterioration of the liquid.

In addition, in the first to sixth embodiments, the liquid level gauge 20 being an example of the accommodation unit includes the liquid level gauge main body 21 having a substantially rectangular parallelepiped shape, but the accommodation unit is not limited thereto. For example, the liquid level gauge 20 or 230 being an example of the accommodation unit may include a liquid level gauge main body with a semicircular cross-sectional shape in a cross section orthogonal to the longitudinal direction.

What is claimed is:

1. A hydraulic unit comprising:
   a liquid tank;
   a liquid level gauge having
       an accommodation unit attached to an exterior of the liquid tank, the accommodation unit having a translucent hollow body that defines an interior space of the accommodation unit, and
       a pair of bolts coupled to the accommodation unit to attach the accommodation unit to the exterior of the liquid tank, the bolts each having a communication path with a first end opening that opens at the interior space of the accommodation unit and a second end opening that opens at an interior space of the liquid tank such that a liquid is introduced into the interior space of the accommodation unit from the liquid tank; and
   a liquid sensor having
       a light receiver configured to receive light, the light receiver being attached to an outside of the accommodation unit, the light receiver being configured
           to receive light that has passed through the liquid in the accommodation unit or light reflected by the liquid, and
           to output a signal related to a physical quantity of the liquid,
       a power source that is rechargeable, the power source being configured to supply electric power to the light receiver, and
       a thermoelectric conversion element configured to generate electric power to charge the power source, the thermoelectric conversion element being in contact with a head portion of one of the bolts.

2. The hydraulic unit according to claim 1, wherein the signal related to the physical quantity of the liquid includes a signal related to presence or absence of the liquid in the accommodation unit.

3. The hydraulic unit according to claim 2, wherein the accommodation unit includes a float disposed inside the translucent hollow body.

4. The liquid sensor hydraulic unit according to claim 2, wherein the liquid sensor has a wireless transmitter configured
   to be supplied with electric power from the power source and
   to transmit the signal related to the physical quantity of the liquid to outside.

5. The hydraulic unit according to claim 1, wherein the liquid sensor has a casing attached to the outside of the accommodation unit such that the casing is entirely located outside of the liquid tank, the light receiver being provided in the casing.

6. The hydraulic unit according to claim 2, wherein the liquid sensor has a casing attached to the outside of the accommodation unit and being in contact with the accommodation unit to be held by the accommodation unit.

7. The hydraulic unit according to claim 2, wherein the signal related to the physical quantity of the liquid includes a signal related to a deterioration degree of the liquid.

8. The hydraulic unit according to claim 7, wherein the signal related to the physical quantity of the liquid includes a signal related to a hue of
   light that has passed through the liquid and has been received by the light receiver or
   light that has been reflected by the liquid and has been received by the light receiver, and
   the deterioration degree of the liquid is determined from the hue.

9. The hydraulic unit according to claim 2, wherein
the liquid sensor has a light emitter configured to emit
    light, the light emitter being attachable to the outside of
    the accommodation unit,
the light receiver being configured to receive
    light emitted by the light emitter and having passed
        through the liquid in the accommodation unit or
    light emitted by the light emitter and having been
        reflected by the liquid in the accommodation unit.
10. The hydraulic unit according to claim 9, wherein
the light emitter and the light receiver are arranged to face
    each other across the accommodation unit, and
the light receiver is configured to receive light that has
    passed through the liquid in the accommodation unit.
11. The hydraulic unit according to claim 9, wherein
the light emitter and the light receiver are arranged on a
    same side of the accommodation unit, and
the light receiver is configured to receive light that has
    been reflected by the liquid in the accommodation unit.
12. The hydraulic unit according to claim 9, wherein
the liquid sensor has a casing attached to the outside of the
    accommodation unit,
the light emitter and the light receiver being integrally
    provided in the casing.
13. A liquid sensor comprising:
a light receiver configured to receive light, the light
    receiver being configured to be attached to an outside
    of an accommodation unit into which a liquid is intro-
    duced and which has translucency; and
a light emitter configured to emit light, the light emitter
    being configured to be attached to the outside of the
    accommodation unit,
the light receiver being configured
    to receive light that is emitted by the light emitter and
        has passed through the liquid in the accommodation
        unit when the light emitter faces the light receiver of
        light that is emitted by the light emitter and is
        reflected by the liquid in the accommodation unit,
        and

16 to output a signal related to a physical quantity of the
        liquid,
the accommodation unit being located outside of a liquid
    tank from which the liquid is introduced into the
    accommodation unit,
the signal related to the physical quantity of the liquid
    including a signal indicating whether the liquid is
    present or absent in the accommodation unit, and
the light emitter being configured to change state from off
    to on or emission color according to the signal indi-
    cating that the liquid is absent in the accommodation
    unit.
14. The liquid sensor according to claim 13, wherein
the accommodation unit is a liquid level gauge.
15. A liquid sensor comprising:
a light receiver configured to receive light, the light
    receiver being configured to be attached to an outside
    of an accommodation unit into which a liquid is intro-
    duced and which has translucency; and
a light emitter configured to emit light, the light emitter
    being configured to be attached to the outside of the
    accommodation unit,
the light receiver being configured
    to receive light that is emitted by the light emitter and
        has passed through the liquid in the accommodation
        unit when the light emitter faces the light receiver or
        light that is emitted by the light emitter and is
        reflected by the liquid in the accommodation unit,
        and
    to output a signal related to a physical quantity of the
        liquid,
the accommodation unit being located outside of a liquid
    tank from which the liquid is introduced into the
    accommodation unit,
the light emitter being configured to change state from off
    to blinking according to the signal related to the physi-
    cal quantity of the liquid.

* * * * *